US009962189B2

(12) United States Patent
Mirkovic et al.

(10) Patent No.: US 9,962,189 B2
(45) Date of Patent: *May 8, 2018

(54) METHOD AND APPARATUS FOR SPINAL STABILIZATION

(71) Applicant: Decima Spine, Inc., San Juan, PR (US)

(72) Inventors: Srdjan Mirkovic, Northfield, IL (US); Brad S. Culbert, Rancho Santa Margarita, CA (US)

(73) Assignee: Decima Spine, Inc., San Juan, PR (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/238,121

(22) Filed: Aug. 16, 2016

(65) Prior Publication Data

US 2017/0065301 A1 Mar. 9, 2017

Related U.S. Application Data

(60) Continuation of application No. 12/686,262, filed on Jan. 12, 2010, now Pat. No. 9,445,826, which is a
(Continued)

(51) Int. Cl.
*A61B 17/70* (2006.01)
*A61B 17/16* (2006.01)
*A61B 17/86* (2006.01)

(52) U.S. Cl.
CPC .......... *A61B 17/70* (2013.01); *A61B 17/1637* (2013.01); *A61B 17/1671* (2013.01); *A61B 17/8685* (2013.01)

(58) Field of Classification Search
CPC . A61B 17/70; A61B 17/1637; A61B 17/1671; A61B 17/8685
(Continued)

(56) References Cited

U.S. PATENT DOCUMENTS

| 2,570,465 A | 10/1951 | Lundholm |
| 4,456,005 A | 6/1984 | Lichty |

(Continued)

FOREIGN PATENT DOCUMENTS

| EP | 0 625 336 | 11/1994 |
| JP | 6-319742 A | 11/1994 |

(Continued)

OTHER PUBLICATIONS

Apr. 13, 2006 International Search Report for App. No. PCT/US2005/044321.
(Continued)

*Primary Examiner* — Pedro Philogene
*Assistant Examiner* — David C Comstock
(74) *Attorney, Agent, or Firm* — Knobbe, Martens, Olson & Bear, LLP

(57) ABSTRACT

A method of limiting at least one degree of movement between a superior vertebral body and an inferior vertebral body of a patient includes advancing a distal end of a stabilization device into a pedicle of the inferior vertebral body. A proximal portion of the stabilization device is positioned such that the proximal portion limits at least one degree of movement between a superior vertebral body and an inferior vertebral body by contacting a surface of the superior vertebral body.

20 Claims, 11 Drawing Sheets

Related U.S. Application Data division of application No. 11/056,991, filed on Feb. 11, 2005, now Pat. No. 7,648,523.

(60) Provisional application No. 60/634,203, filed on Dec. 8, 2004.

(58) Field of Classification Search
USPC .................................................. 606/246–249
See application file for complete search history.

(56) References Cited

U.S. PATENT DOCUMENTS

| | | |
|---|---|---|
| 4,532,660 A | 8/1985 | Field |
| 4,796,612 A | 1/1989 | Reese |
| 4,940,467 A | 7/1990 | Tronzo |
| 5,116,336 A | 5/1992 | Frigg |
| 5,122,133 A | 6/1992 | Evans |
| 5,167,664 A | 12/1992 | Hodorek |
| 5,217,462 A | 6/1993 | Asnis et al. |
| 5,334,184 A | 8/1994 | Bimman |
| 5,382,248 A | 1/1995 | Jacobson et al. |
| 5,387,213 A | 2/1995 | Breard et al. |
| 5,415,661 A | 5/1995 | Holmes |
| 5,470,333 A | 11/1995 | Ray |
| 5,496,318 A | 3/1996 | Howland et al. |
| 5,498,265 A | 3/1996 | Asnis et al. |
| 5,520,690 A | 5/1996 | Errico et al. |
| 5,527,312 A | 6/1996 | Ray |
| 5,540,688 A | 7/1996 | Navas |
| 5,558,674 A | 9/1996 | Heggeness et al. |
| 5,569,248 A | 10/1996 | Mathews |
| 5,569,548 A | 10/1996 | Koike et al. |
| 5,609,634 A | 3/1997 | Voydeville |
| 5,645,599 A | 7/1997 | Samani |
| 5,667,508 A | 9/1997 | Errico et al. |
| 5,893,850 A | 4/1999 | Cachia |
| 5,989,255 A | 11/1999 | Pepper et al. |
| 5,997,538 A | 12/1999 | Asnis et al. |
| 6,004,327 A | 12/1999 | Asnis et al. |
| 6,048,342 A | 4/2000 | Zucherman et al. |
| 6,051,007 A | 4/2000 | Hogendijk et al. |
| 6,102,914 A | 8/2000 | Bulstra et al. |
| 6,127,597 A | 10/2000 | Beyar et al. |
| 6,248,108 B1 | 6/2001 | Tormala et al. |
| 6,287,313 B1 | 9/2001 | Sasso |
| 6,361,538 B1 | 3/2002 | Fenaroli et al. |
| 6,379,355 B1 | 4/2002 | Zucherman et al. |
| 6,440,169 B1 | 8/2002 | Elberg et al. |
| 6,485,518 B1 | 11/2002 | Cornwall et al. |
| 6,511,481 B2 | 1/2003 | von Hoffmann et al. |
| 6,540,747 B1 | 4/2003 | Marino |
| 6,547,795 B2 | 4/2003 | Schneiderman |
| 6,562,046 B2 | 5/2003 | Sasso |
| 6,610,091 B1 | 8/2003 | Reiley |
| 6,613,050 B1 | 9/2003 | Wagner et al. |
| 6,626,944 B1 | 9/2003 | Taylor |
| 6,632,224 B2 | 10/2003 | Cachia et al. |
| 6,648,890 B2 | 11/2003 | Culbert et al. |
| 6,648,893 B2 | 11/2003 | Dudasik |
| 6,669,698 B1 | 12/2003 | Tromanhauser et al. |
| 6,669,729 B2 | 12/2003 | Chin |
| 6,733,534 B2 | 5/2004 | Sherman |
| 6,752,831 B2 | 6/2004 | Sybert et al. |
| 6,761,720 B1 | 7/2004 | Senegas |
| 6,770,075 B2 | 8/2004 | Howland |
| 6,793,656 B1 | 9/2004 | Mathews |
| 6,796,983 B1 | 9/2004 | Zucherman et al. |
| 6,808,526 B1 | 10/2004 | Magerl et al. |
| 6,835,205 B2 | 12/2004 | Atkinson et al. |
| 6,887,243 B2 | 5/2005 | Culbert et al. |
| 6,890,333 B2 | 5/2005 | von Hoffmann et al. |
| 6,908,465 B2 | 6/2005 | von Hoffmann et al. |
| 6,921,403 B2 | 6/2005 | Cragg et al. |
| 6,932,820 B2 | 8/2005 | Osman |
| 6,942,668 B2 | 9/2005 | Padget et al. |
| 6,945,975 B2 | 9/2005 | Dalton |
| 6,951,561 B2 | 10/2005 | Warren et al. |
| 6,974,478 B2 | 12/2005 | Reiley et al. |
| 7,060,068 B2 | 6/2006 | Tromanhauser et al. |
| 7,070,601 B2 | 7/2006 | Culbert et al. |
| 7,074,203 B1 | 7/2006 | Johanson et al. |
| 7,371,238 B2 | 5/2008 | Soboleski et al. |
| 7,556,629 B2 | 7/2009 | von Hoffmann et al. |
| 7,648,523 B2 | 1/2010 | Mirkovic et al. |
| 7,824,429 B2 | 11/2010 | Culbert et al. |
| 7,846,183 B2 | 12/2010 | Blain |
| 7,857,832 B2 | 12/2010 | Culbert et al. |
| 7,901,438 B2 | 3/2011 | Culbert et al. |
| 7,938,832 B2 | 5/2011 | Culbert et al. |
| 7,993,377 B2 | 8/2011 | Culbert et al. |
| 7,998,176 B2 | 8/2011 | Culbert |
| 8,109,977 B2 | 2/2012 | Culbert et al. |
| 8,556,949 B2 | 10/2013 | Teisen et al. |
| 8,652,183 B1 | 2/2014 | Truman |
| 9,226,758 B2 | 1/2016 | Culbert et al. |
| 9,445,826 B2 * | 9/2016 | Mirkovic |
| 2002/0143331 A1 | 10/2002 | Zucherman et al. |
| 2002/0143335 A1 | 10/2002 | von Hoffmann et al. |
| 2002/0151895 A1 | 10/2002 | Soboleski et al. |
| 2002/0198526 A1 | 12/2002 | Shaolian et al. |
| 2003/0028250 A1 | 2/2003 | Reiley et al. |
| 2003/0065330 A1 | 4/2003 | Zucherman et al. |
| 2003/0069582 A1 | 4/2003 | Culbert et al. |
| 2003/0220643 A1 | 11/2003 | Ferree |
| 2004/0006391 A1 | 1/2004 | Reiley |
| 2004/0049190 A1 | 3/2004 | Biedermann et al. |
| 2004/0097941 A1 | 5/2004 | Weiner et al. |
| 2004/0127906 A1 | 7/2004 | Culbert et al. |
| 2004/0199162 A1 | 10/2004 | von Hoffmann et al. |
| 2004/0225292 A1 | 11/2004 | Sasso et al. |
| 2004/0254575 A1 | 12/2004 | Obenchain et al. |
| 2005/0033434 A1 | 2/2005 | Berry |
| 2005/0090833 A1 | 4/2005 | Di Poto |
| 2005/0119657 A1 | 6/2005 | Goldsmith |
| 2005/0131411 A1 | 6/2005 | Culbert et al. |
| 2005/0137595 A1 | 6/2005 | von Hoffmann et al. |
| 2005/0143734 A1 | 6/2005 | Cachia et al. |
| 2005/0149030 A1 | 7/2005 | Serhan |
| 2005/0177240 A1 | 8/2005 | Blain |
| 2005/0216026 A1 | 9/2005 | Culbert |
| 2005/0251142 A1 | 11/2005 | von Hoffmann et al. |
| 2005/0283238 A1 | 12/2005 | Reiley |
| 2006/0015105 A1 | 1/2006 | Warren et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0058790 A1 | 3/2006 | Carl et al. |
| 2006/0079908 A1 | 4/2006 | Lieberman |
| 2006/0084977 A1 | 4/2006 | Lieberman |
| 2006/0084983 A1 | 4/2006 | Kim |
| 2006/0085010 A1 | 4/2006 | Lieberman |
| 2006/0100707 A1 | 5/2006 | Stinson et al. |
| 2006/0122609 A1 | 6/2006 | Mirkovic et al. |
| 2006/0122610 A1 | 6/2006 | Culbert et al. |
| 2006/0195103 A1 | 8/2006 | Padget et al. |
| 2007/0016191 A1 | 1/2007 | Culbert et al. |
| 2007/0118132 A1 | 5/2007 | Culbert et al. |
| 2007/0123868 A1 | 5/2007 | Culbert et al. |
| 2008/0097436 A1 | 4/2008 | Culbert et al. |
| 2008/0221623 A1 | 9/2008 | Gooch |
| 2008/0306537 A1 | 12/2008 | Culbert et al. |
| 2010/0174314 A1 | 7/2010 | Mirkovic |
| 2010/0217330 A1 | 8/2010 | Phan et al. |
| 2013/0096634 A1 | 4/2013 | Suh |

FOREIGN PATENT DOCUMENTS

| | | |
|---|---|---|
| WO | WO 00/67652 | 5/2000 |
| WO | WO 2001/54598 | 8/2001 |
| WO | WO 2003/043488 | 5/2003 |
| WO | WO 2004/008949 | 1/2004 |
| WO | WO 2004/078220 | 9/2004 |

(56) References Cited

FOREIGN PATENT DOCUMENTS

| WO | WO 2005/112835 | 12/2005 |
|----|----|----|
| WO | WO 2006/063083 | 6/2006 |
| WO | WO 2007/124130 | 4/2008 |
| WO | WO 2009/047630 | 4/2009 |

OTHER PUBLICATIONS

Apr. 19, 2007 Office Action for European Application No. 02 719 402.6 filed Mar. 29, 2002.
Sep. 7, 2009 Office Action for European Application No. 05 853 282.1filed Dec. 8, 2005.
Jan. 27, 2011 Office Action for Australian Application No. 2005314079 filed Dec. 8, 2005.
Jul. 5, 2011 Office Action (Rejection Notice dispatched Jul. 13, 2011) for Japanese Application No. 2007-545602.

* cited by examiner

METHOD AND APPARATUS FOR SPINAL STABILIZATION

PRIORITY INFORMATION

This application is a continuation of U.S. patent application Ser. No. 12/686,262, filed Jan. 12, 2010, which is a divisional of U.S. patent application Ser. No. 11/056,991, filed Feb. 11, 2005, which claims the priority benefit under 35 U.S.C. § 119(e) of Provisional Application 60/634,203 filed Dec. 8, 2004, the disclosures of each of these applications are hereby incorporated by reference herein in their entirety.

BACKGROUND OF THE INVENTION

Field of the Invention

The present invention relates to medical devices and, more particularly, to methods and apparatuses for spinal stabilization.

Description of the Related Art

The human spine is a flexible weight bearing column formed from a plurality of bones called vertebrae. There are thirty three vertebrae, which can be grouped into one of five regions (cervical, thoracic, lumbar, sacral, and coccygeal). Moving down the spine, there are generally seven cervical vertebra, twelve thoracic vertebra, five lumbar vertebra, five sacral vertebra, and four coccygeal vertebra. The vertebra of the cervical, thoracic, and lumbar regions of the spine are typically separate throughout the life of an individual. In contrast, the vertebra of the sacral and coccygeal regions in an adult are fused to form two bones, the five sacral vertebra which form the sacrum and the four coccygeal vertebra which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Spinal fusion is one such method. In spinal fusion, one or more of the vertebra of the spine are united together ("fused") so that motion no longer occurs between them. The vertebra may be united with various types of fixation systems. These fixation systems may include a variety of longitudinal elements such as rods or plates that span two or more vertebrae and are affixed to the vertebrae by various fixation elements such as wires, staples, and screws (often inserted through the pedicles of the vertebrae). These systems may be affixed to either the posterior or the anterior side of the spine. In other applications, one or more bone screws may be inserted through adjacent vertebrae to provide stabilization.

Although spinal fusion is a highly documented and proven form of treatment in many patients, there is currently a great interest in surgical techniques that provide stabilization of the spine while allowing for some degree of movement. In this manner, the natural motion of the spine can be preserved, especially for those patients with mild or moderate disc conditions. In certain of these techniques, flexible materials are used as fixation rods to stabilize the spine while permitting a limited degree of movement.

Notwithstanding the variety of efforts in the prior art described above, these techniques are associated with a variety of disadvantages. In particular, these techniques typically involve an open surgical procedure, which results higher cost, lengthy in-patient hospital stays and the pain associated with open procedures.

Therefore, there remains a need for improved techniques and systems for stabilization the spine. Preferably, the devices are implantable through a minimally invasive procedure.

SUMMARY OF THE INVENTION

Accordingly, one embodiment of the present invention comprises a method of limiting at least one degree of movement between a superior vertebral body and an inferior vertebral body of a patient. A distal end of a stabilization device is advanced into a pedicle of the inferior vertebral body. A proximal portion of the stabilization device is positioned such that the proximal portion limits at least one degree of movement between a superior vertebral body and an inferior vertebral body by contacting a surface of the superior vertebral body.

Another embodiment of the present invention also comprises a method of limiting at least one degree of movement between a superior vertebral body and an inferior vertebral body of a patient. A distal end of a first stabilization device is advanced into a pedicle of the inferior vertebral body. A proximal portion of the first stabilization device is positioned such that the proximal portion abuts against a surface of an inferior articular process of the superior adjacent vertebral body to limit at least one degree of movement between a superior vertebral body and an inferior vertebral body. A distal end of a second stabilization device is advanced into a pedicle of the inferior vertebral body such that it is positioned with bilateral symmetry with respect to the first stabilization device. A proximal portion of the second stabilization device is positioned such that the proximal portion abuts, with bilateral symmetry with respect to the first stabilization device, against a surface of a second inferior articular process of the superior adjacent vertebral body to limit at least one degree of movement between the superior vertebral body and the inferior vertebral body.

Another embodiment of the present invention comprises a spinal stabilization device that includes an elongate body, having a proximal end and a distal end. A distal anchor is on the distal end of the elongate body. A retention structure is on the body, proximal to the distal anchor. A proximal anchor is moveably carried by the body. The proximal anchor has an outer surface with at least a portion of the outer surface being elastic. At least one complementary retention structure on the proximal anchor configured for permitting proximal movement of the body with respect to the proximal anchor but resisting distal movement of the body with respect the proximal anchor.

Another embodiment of the present invention comprises a spinal stabilization device for limiting at least one degree of movement between a superior vertebral body and an inferior vertebral body of a patient. The device includes an elongate body that has a proximal end and a distal end. A distal anchor is positioned on the distal end of the elongate body. A retention structure is on the body, proximal to the distal anchor. A proximal anchor is moveably carried by the body. The proximal anchor includes at least one flat surface configured to abut against a surface of the inferior articular process of the superior adjacent vertebral body when the stabilization device is inserted into the inferior adjacent vertebral body. At least one complementary retention structure is on the proximal anchor and is configured for permitting proximal movement of the body with respect to the proximal anchor but resisting distal movement of the body with respect the proximal anchor.

Yet another embodiment of the present invention comprises a spinal stabilization device for limiting at least one degree of movement between a superior vertebral body and an inferior vertebral body of a patient. The device comprises an elongate body, having a proximal end and a distal end. A distal anchor is on the distal end of the elongate body. A retention structure is positioned on the body, proximal to the distal anchor. A proximal anchor is moveably carried by the body. The proximal anchor includes at least one saddle-shaped surface configured to abut against an inferior articular process of the superior adjacent vertebral body when the stabilization device is inserted into the inferior adjacent vertebral body. At least one complementary retention structure is on the proximal anchor and is configured for permitting proximal movement of the body with respect to the proximal anchor but resisting distal movement of the body with respect the proximal anchor.

DETAILED DESCRIPTION OF THE PREFERRED EMBODIMENTS

Although the stabilization devices of the present invention will be disclosed primarily in the context of a spinal stabilization procedure, the methods and structures disclosed herein are intended for application in any of a variety medical applications, as will be apparent to those of skill in the art in view of the disclosure herein. For example, certain features and aspects of bone stabilization device and techniques described herein may be applicable to proximal fractures of the femur and a wide variety of fractures and osteotomies, the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. See e.g., U.S. Pat. No. 6,511,481, which is hereby incorporated by reference herein. A wide variety of phalangeal and metatarsal osteotomies and fractures of the foot may also be stabilized using the bone fixation devices described herein. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. Fractures of the fibular and tibial malleoli, pilon fractures and other fractures of the bones of the leg may be fixated and stabilized with these bone fixation devices with or without the use of plates, both absorbable or non-absorbing types, and with alternate embodiments of the current invention The stabilization devices may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The stabilization devices may also be used to attach sutures to the bone, such as in any of a variety of tissue suspension procedures. The bone stabilization device described herein may be used with or without plate(s) or washer(s), all of which can be either permanent, absorbable, or combinations.

Figure 1A:
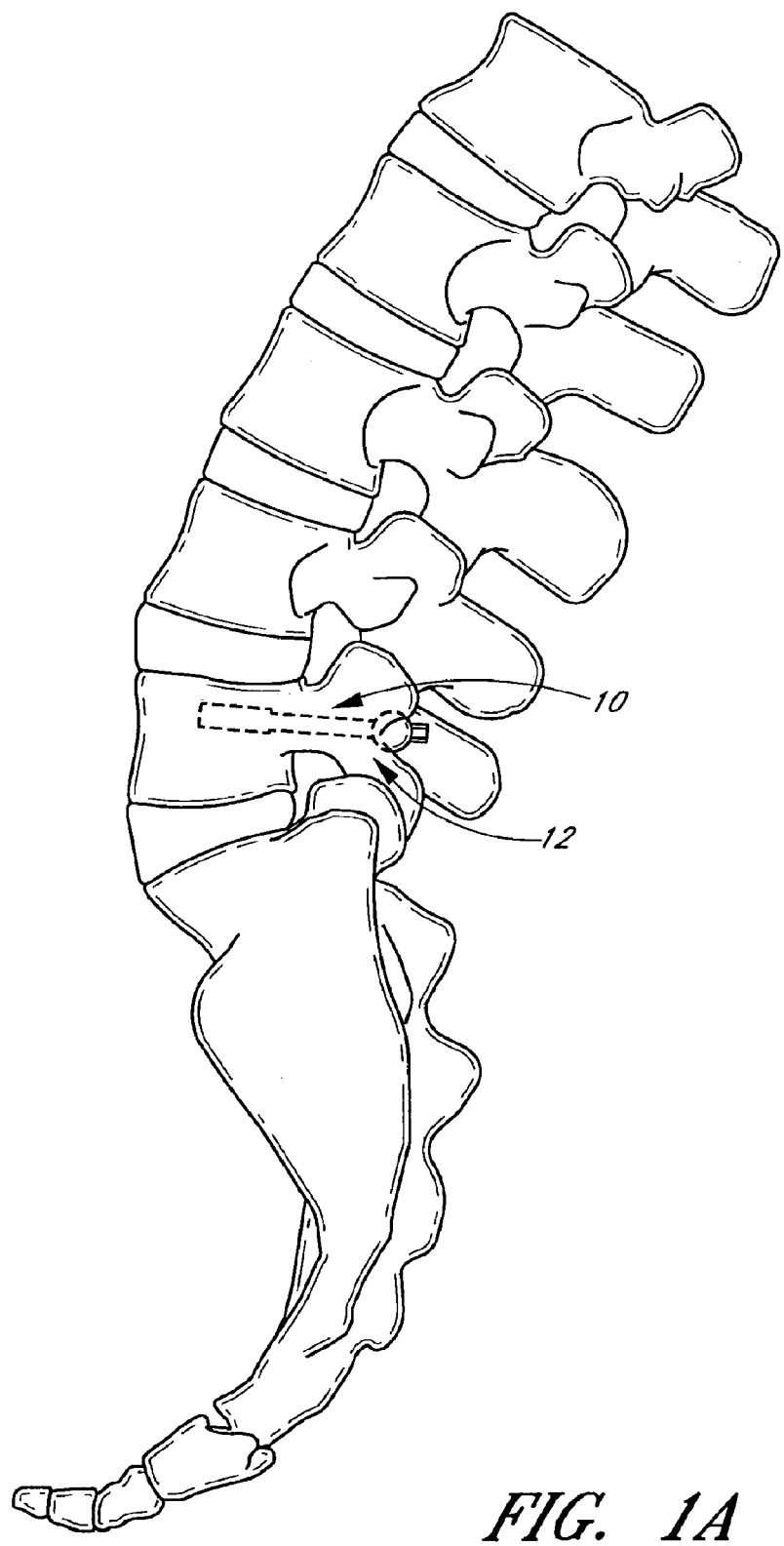
FIG. 1A a side elevational view of a portion of a vertebra having an exemplary embodiment of a stabilization device implanted therein.
Figure 1B:
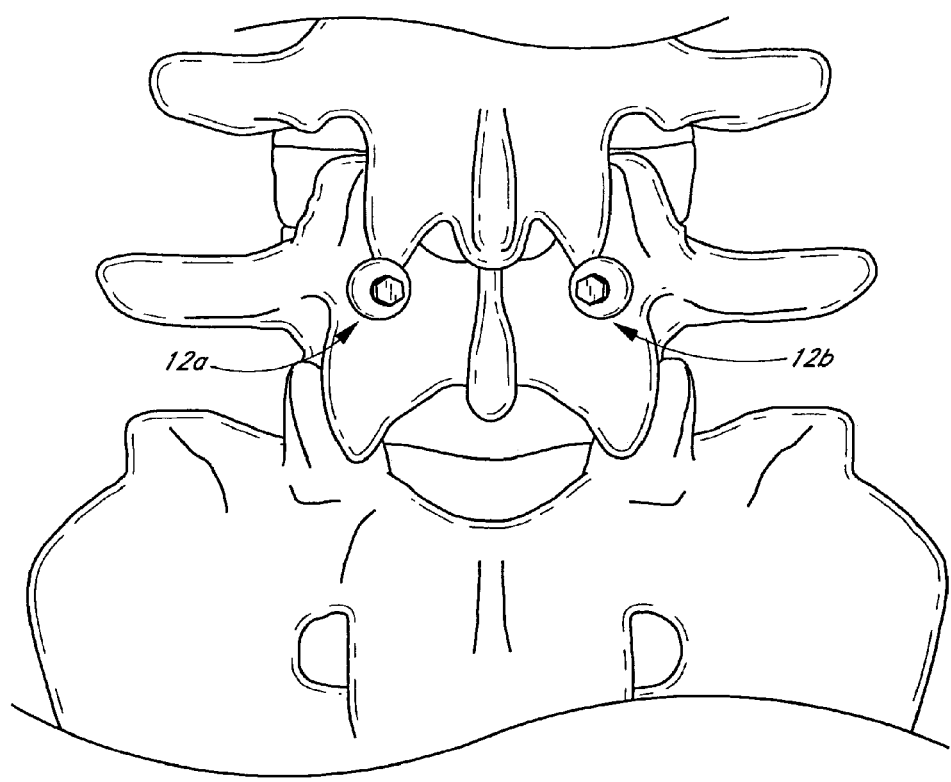
FIG. 1B is a posterior view of a portion of a vertebra having two devices similar to that of FIG. 1A implanted bilaterally therein.

FIGS. 1A and 1B are side and rear elevational views of a pair of bone stabilization devices 12, positioned within a vertebra 10 of the spine. As will be explained in more detail below, the bone stabilization devices 12 may be used in a variety of techniques to stabilize the spine. For example, in the illustrated embodiment, the distal end of the bone stabilization device 12 is inserted into the pedicle of the vertebrae, preferably through the pars (i.e., the region of the lamina between the superior and inferior articular processes). The proximal end of the device 12 extends above the pars such that it limits motion of the superior adjacent vertebrae with respect to the inferior articular process. In one embodiment, the proximal end of the device limits motion by abutting and/or wedging against a surface of the superior adjacent vertebrae as the superior adjacent vertebrae moves relative to the inferior adjacent vertebrae. In this manner, at least one degree of motion between the inferior and superior vertebrae may be limited. As explained below, the bone stabilization devices 12 may be used after laminectomy, discectomy, artificial disc replacement, and other applications for providing temporary or permanent stability in the spinal column. For example, lateral or central spinal stenosis may be treated with the bone fixation devices 12 and techniques described below. In such procedures, the bone fixation devices 12 and techniques may be used alone or in combination with laminectomy, discectomy, artificial disc replacement, and/or other applications for relieving pain and/or providing stability.

An embodiment of the stabilization device 12 will now be described in detail with initial reference to FIGS. 2-4. The stabilization device 12 comprises a body 28 that extends between a proximal end 30 and a distal end 32. The length, diameter and construction materials of the body 28 can be varied, depending upon the intended clinical application. In embodiments optimized for spinal stabilization in an adult human population, the body 28 will generally be within the range of from about 20-90 mm in length and within the range of from about 3.0-8.5 mm in maximum diameter. The length of the helical anchor, discussed below, may be about 8-80 millimeters. Of course, it is understood that these dimensions are illustrative and that they may be varied as required for a particular patient or procedure.

In one embodiment, the body 28 comprises titanium. However, as will be described in more detail below, other metals, or bioabsorbable or nonabsorbable polymeric materials may be utilized, depending upon the dimensions and desired structural integrity of the finished stabilization device 12.

The distal end 32 of the body 28 is provided with a cancellous bone anchor or distal cortical bone anchor 34. Generally, for spinal stabilization, the distal bone anchor 34 is adapted to be rotationally inserted into a portion (e.g., the facet or pedicle) of a first vertebra. In the illustrated embodiment, the distal anchor 34 comprises a helical locking structure 72 for engaging cancellous and/or distal cortical bone. In the illustrated embodiment, the locking structure 72 comprises a flange that is wrapped around a central core 73, which in the illustrated embodiment is generally cylindrical in shape. The flange 72 extends through at least one and generally from about two to about 50 or more full revolutions depending upon the axial length of the distal anchor 34 and intended application. The flange will generally complete from about 2 to about 20 revolutions. The helical flange 72 is preferably provided with a pitch and an axial spacing to optimize the retention force within cancellous bone.

Figure 3:
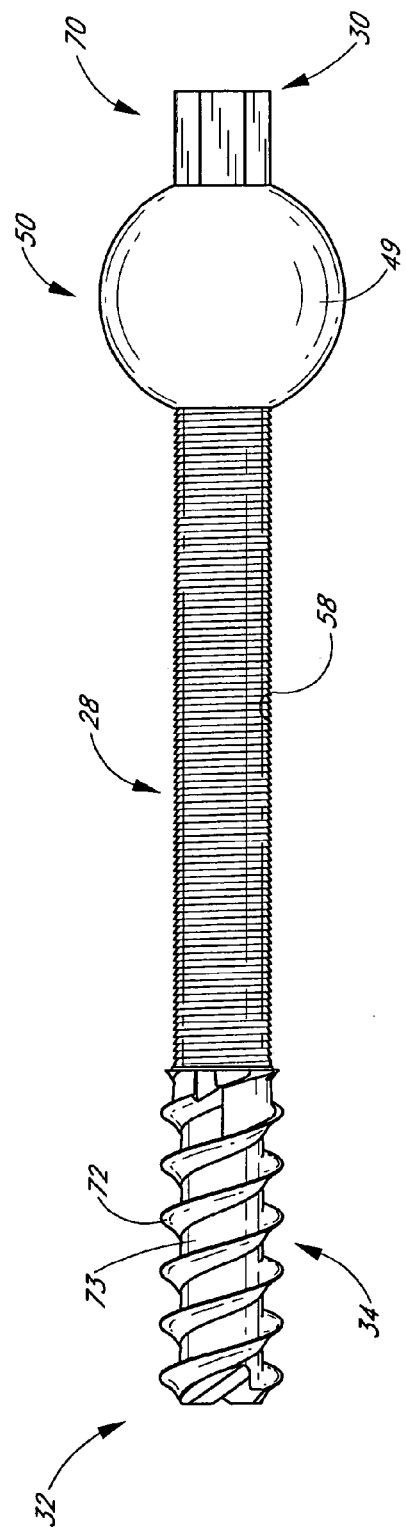
FIG. 3 is a side view of the stabilization device of FIG. 2.

The helical flange 72 of the illustrated embodiment has a generally triangular cross-sectional shape (see FIG. 3). However, it should be appreciated that the helical flange 72 can have any of a variety of cross sectional shapes, such as rectangular, oval or other as deemed desirable for a particular application through routine experimentation in view of the disclosure herein. For example, in one modified embodiment, the flange 72 has a triangular cross-sectional shape with a blunted or square apex. The outer edge of the helical flange 72 defines an outer boundary. The ratio of the diameter of the outer boundary to the diameter of the central core 73 can be optimized with respect to the desired retention force within the cancellous bone and giving due consideration to the structural integrity and strength of the distal anchor 34. Another aspect of the distal anchor 34 that can be optimized is the shape of the outer boundary and the central core 73, which in the illustrated embodiment are generally cylindrical.

The distal end 32 and/or the outer edges of the helical flange 72 may be atraumatic (e.g., blunt or soft). This inhibits the tendency of the stabilization device 12 to migrate anatomically distally and potentially out of the vertebrae after implantation. Distal migration is also inhibited by the dimensions and presence of a proximal anchor 50, which will be described below. In the spinal column, distal migration is particularly disadvantageous because the distal anchor 34 may harm the tissue, nerves, blood vessels and/or spinal cord which lie within and/or surround the spine. In other embodiments, the distal end 32 and/or the outer edges of the helical flange 72 may be sharp and/or configured such that the distal anchor 34 is self tapping and/or self drilling.

A variety of other embodiments for the distal anchor 32 can also be used. For example, the various distal anchors described in co-pending U.S. patent application Ser. No. 10/012,687, filed Nov. 13, 2001 can be incorporated into the stabilization device 12 described herein. The entire contents of this application are hereby expressly incorporated by reference. In particular, the distal anchor 32 may comprise a single helical thread surrounding a lumen, much as in a conventional corkscrew. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal bone, and whether the distal anchor is intended to engage exclusively cancellous bone or will also engage cortical bone. In still other embodiments, the distal anchor 34 may be formed without a helical flange. For example, various embodiments of levers, prongs, hooks and/or radially expandable devices may also be used. See e.g., U.S. Pat. No. 6,648,890, which is hereby expressly incorporated by reference in its entirety.

Figure 3A:
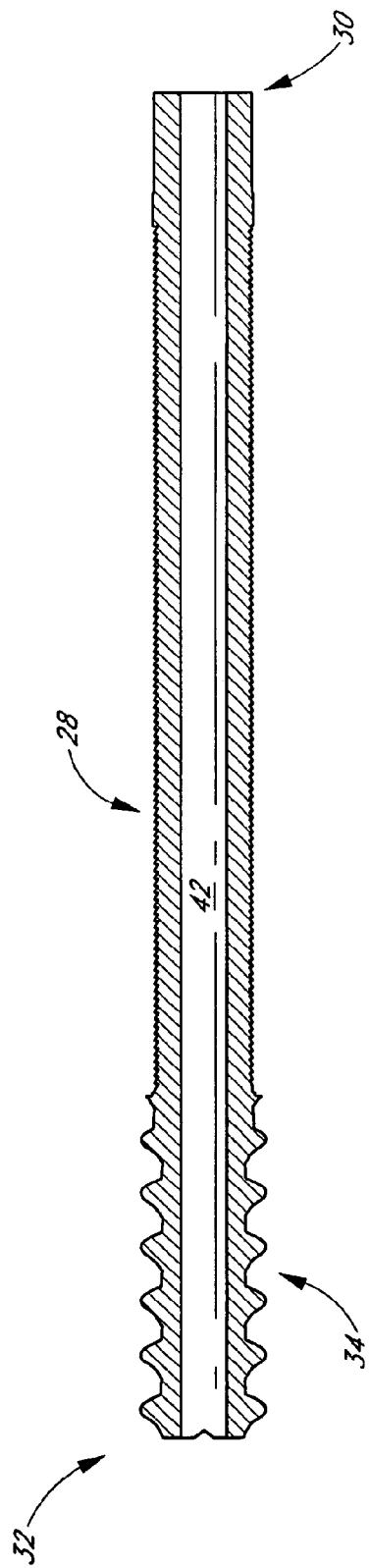
FIG. 3A is a cross-sectional view of a body portion of the stabilization device of FIG. 2.

As shown in FIG. 3A, the body 28 is cannulated forming a central lumen 42 to accommodate installation over a placement wire as is understood in the art. The cross section of the illustrated central lumen is circular but in other embodiments may be non circular, e.g., hexagonal, to accommodate a corresponding male tool for installation or removal of the body 28 as explained below. In other embodiments, the body 28 may partially or wholly solid.

Figure 2:
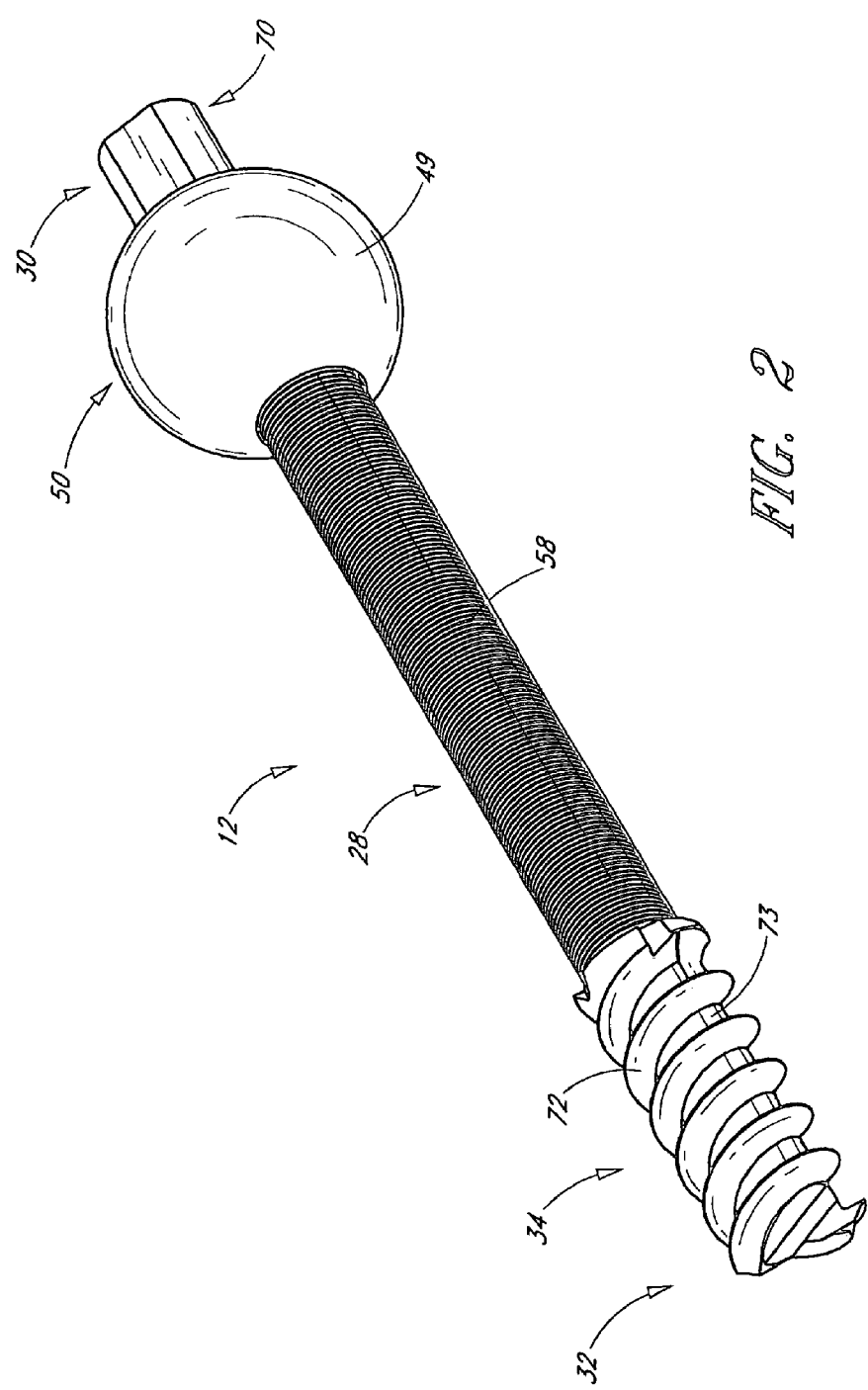
FIG. 2 is a side perspective view of the stabilization device of FIGS. 1A and 1B.
Figure 4:
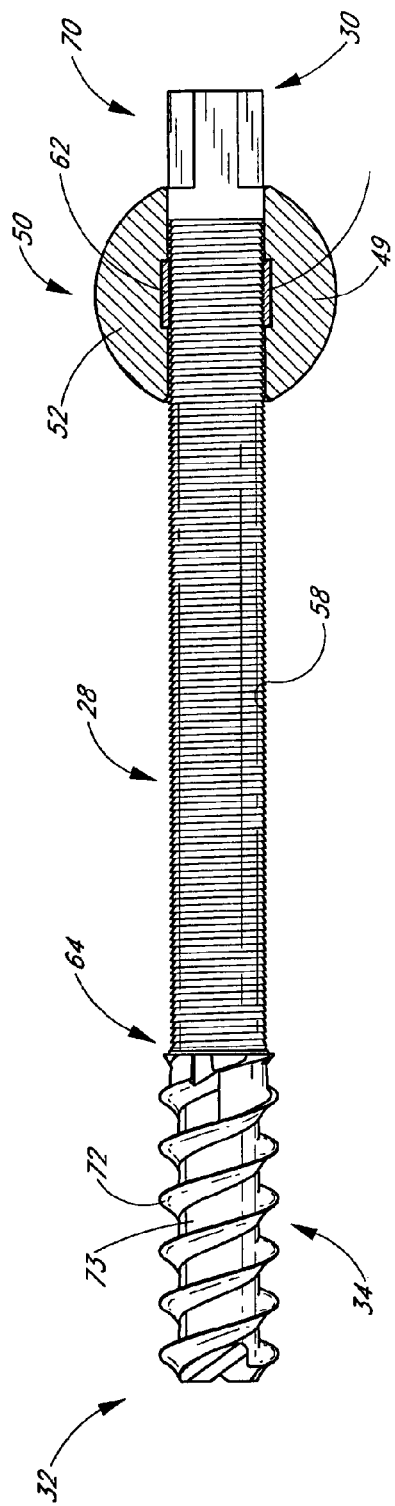
FIG. 4 is a partial cross-sectional view of a proximal portion of the stabilization device of FIG. 2.

With continued reference to FIGS. 2-4, the proximal end 30 of the body 28 is provided with a rotational coupling 70, for allowing the body 28 to be rotated. Rotation of the rotational coupling 70 can be utilized to rotationally drive the distal anchor 32 into the bone. In such embodiments, any of a variety of rotation devices may be utilized, such as electric drills or hand tools, which allow the clinician to manually rotate the proximal end 30 of the body 28. Thus, the rotational coupling 70 may have any of a variety of cross sectional configurations, such as one or more curved faces, flats or splines. In the illustrated embodiment, the rotational coupling 70 is a male element in the form of a hexagonal projection. However, in other embodiments, the rotational coupling 70 may be in the form of a female component, machined, milled or attached to the proximal end 30 of the body 28. For example, in one such embodiment, the rotational coupling 70 comprises an axial recess with a polygonal cross section, such as a hexagonal cross section. As explained above, the axial recess may be provided as part of the central lumen 42.

The proximal end 30 of the fixation device is also provided with a proximal anchor 50. The proximal anchor 50 comprises a housing 52, which forms a lumen 53 (see FIG. 5) configured such that the body 28 may extend, at least partially, through the proximal anchor 50. The proximal anchor 50 is axially distally moveable along the body 28, to permit compression of between the distal and proximal ends 32, 30 of the stabilization device 12. As will be explained below, complimentary locking structures such as threads, levers, split rings, and/or ratchet like structures between the proximal anchor 50 and the body 28 resist proximal movement of the anchor 50 with respect to the body 28 under normal use conditions. The proximal anchor 50 preferably can be axially advanced along the body 28 with and/or without rotation as will be apparent from the disclosure herein.

Figure 5:
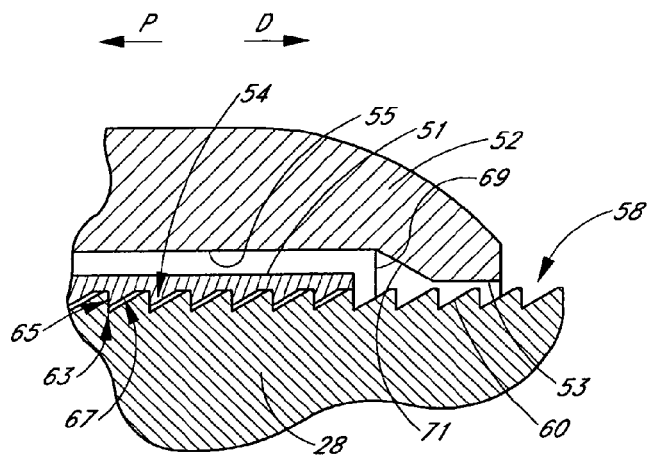
FIG. 5 is an enlarged view of a portion of FIG. 4 labeled 5-5.
Figure 6:
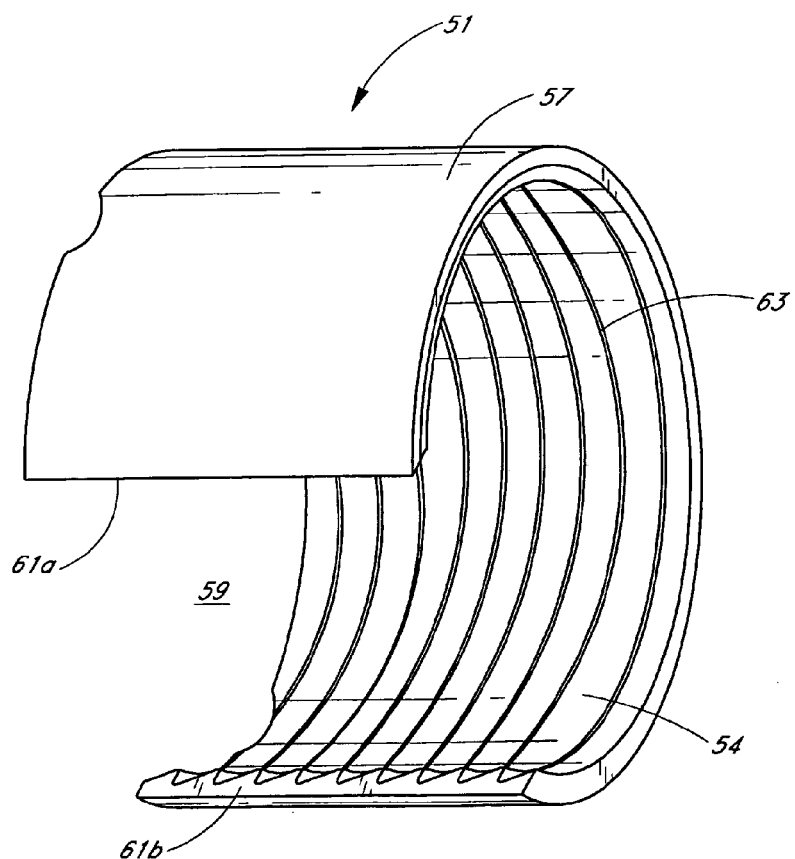
FIG. 6 is a side perspective view of a locking ring of the stabilization device of FIG. 3.

With particular reference to FIGS. 4-6, in the illustrated embodiment, the complementary structure of the proximal anchor 50 is formed by an annular ring 51, which is positioned within an annular recess 55 formed along the lumen 53. As will be explained below, the ring 51 comprises surface structures 54 which interact with complementary surface structures 58 on the body 28. In the illustrated embodiment, the complimentary surface structures 58 comprise a series of annular ridges or grooves 60 formed on the surface of the body 28. The surface structures 54 and complementary surface structures 58 permit distal axial travel of the proximal anchor 50 with respect to the body 28, but resist proximal travel of the proximal anchor 50 with respect to the body 28 as explained below.

As shown in FIG. 6, the annular ring 51 is split (i.e., has a least one gap) and is interposed between the body 28 and the recess 55 of the proximal anchor 50 (see FIG. 5). In the illustrated embodiment, the ring 51 comprises a tubular housing 57 (see FIG. 6), which defines a gap or space 59. In one embodiment, the gap 59 is defined by a pair of edges 61a, 61b, that are generally straight and parallel to each other. Although not illustrated, it should be appreciated that in modified embodiments, the ring 51 can be formed without a gap. When the ring 51 is positioned along the body 28, the ring 51 preferably surrounds a substantial portion of the body 28. The ring 51 can be configured so that the ring 51 can flex or move radially outwardly in response to an axial force so that the ring 51 can be moved relative to the body 28, as described below.

In the illustrated embodiment, the tubular housing 57 includes at least one and in the illustrated embodiment ten teeth or flanges 63, which are configured to engage the complementary surface structures 58 on the body 28 in a ratchet-like motion. In the illustrated embodiment (see FIG. 5), the teeth or flanges include a first surface 65 that lies generally perpendicular to the longitudinal axis of the anchor and generally faces the proximal direction (i.e., the direction labeled "P" in FIG. 5) and a second surface 67 that is inclined with respect to the longitudinal axis of the anchor and that faces distal direction (i.e., the direction labeled "D" in FIG. 5). It should be noted that the proximal and directions in FIG. 5 are reversed with respect to FIG. 4.

With continued reference to FIG. 5, the recess 55 is sized and dimensioned such that as the proximal anchor 50 is advanced distally over the body, the second surface 67 of the annular ring 51 can slide along and over the complementary retention structures 58 of the body 28. That is, the recess 55 provides a space for the annular ring to move radially away from the body 28 as the proximal anchor 50 is advanced distally.

A distal portion 69 of the recess 55 is sized and dimensioned such that after the proximal anchor 50 is appropriately advanced, proximal motion of the proximal anchor 50 is resisted as the annular ring 51 becomes wedged between the body 28 and an angled engagement surface 71 of the distal portion 69. In this manner, proximal movement of the proximal anchor 50 under normal use conditions may be prevented. In modified embodiments, the annular ring 51 can be sized and dimensioned such that the ring 51 is biased inwardly to engage the retention structures 58 on the body 28. The bias of the annular ring 51 can result in a more effective engagement between the complementary retention structures 58 of the body and the retention structures 54 of the ring 51.

As mentioned above, it is contemplated that various other retention structures 54 and complementary retention structures 58 may be used between the body 28 and the proximal anchor 50 to permit distal axial travel of the proximal anchor 50 with respect to the body 28, but resist proximal travel of the proximal anchor 50 with respect to the body 28. Examples of such structures can be found in U.S. Pat. No. 6,685,706, entitled "PROXIMAL ANCHORS FOR BONE FIXATION SYSTEM." The entire contents of this patent is hereby expressly incorporated by reference herein.

As mentioned above, the complimentary surface structures 58 on the body 28 comprise a series of annular ridges or grooves 60. These retention structures 58 are spaced axially apart along the body 28, between a proximal limit 62 and a distal limit 64. See FIG. 4. The axial distance between proximal limit 62 and distal limit 64 is related to the desired axial working range of the proximal anchor 50, and thus the range of functional sizes of the stabilization device 12. Thus, the stabilization device 12 of the exemplary embodiment can provide compression between the distal anchor 34 and the proximal anchor 50 throughout a range of motion following the placement of the distal anchor in a vertebra. That is, the distal anchor 34 may be positioned within the cancellous and/or distal cortical bone of a vertebra, and the proximal anchor may be distally advanced with respect to the distal anchor throughout a range to provide compression without needing to relocate the distal anchor 34 and without needing to initially locate the distal anchor 34 in a precise position with respect to the proximal side of the bone or another vertebra. Providing a working range throughout which tensioning of the proximal anchor 50 is independent from setting the distal anchor 34 allows a single device to be useful for a wide variety of different anatomies, as well as eliminates or reduces the need for accurate device measurement. In addition, this arrangement allows the clinician to adjust the compression force during the procedure without adjusting the position of the distal anchor. In this manner, the clinician may focus on positioning the distal anchor sufficiently within the vertebra to avoid or reduce the potential for distal migration out of the vertebra, which may damage the particularly delicate tissue, blood vessels, nerves and/or spinal cord surrounding or within the spinal column. In addition or alternative, the above described arrangement allows the clinician to adjust the positioning of the proximal anchor 50 with respect to the inferior articular process of the superior adjacent vertebrae. In this manner, the clinician may adjust the position of the proximal anchor 50 without adjusting the position of the distal anchor such that the anchor 50 is configured to wedge or abut against inferior articular process of the superior adjacent vertebrae.

In many applications, the working range is at least about 10% of the overall length of the device, and may be as much as 20% or 50% or more of the overall device length. In the context of a spinal application, working ranges of up to about 10 mm or more may be provided, since estimates within that range can normally be readily accomplished within the clinical setting. The embodiments disclosed herein can be scaled to have a greater or a lesser working range, as will be apparent to those of skill in the art in view of the disclosure herein.

With reference back to FIGS. 2-4, in the illustrated embodiment, the outer surface 49 of the proximal anchor 50 has a smooth or spherical shape. As will be explained below, the outer surface 49 of the proximal anchor 50 is configured to abut against the inferior facet of the superior adjacent vertebrae. In this manner, motion between the adjacent vertebrae may be limited and/or constrained.

Figure 7:
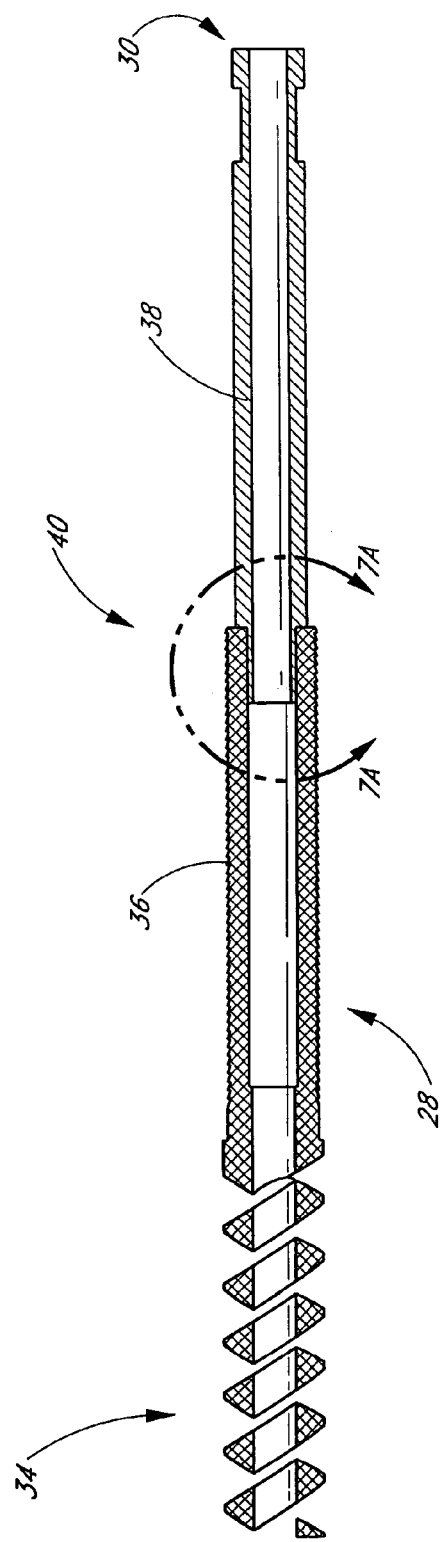
FIG. 7 is a side view of a modified embodiment of a body portion of the stabilization device shown in FIG. 2.
Figure 7A:
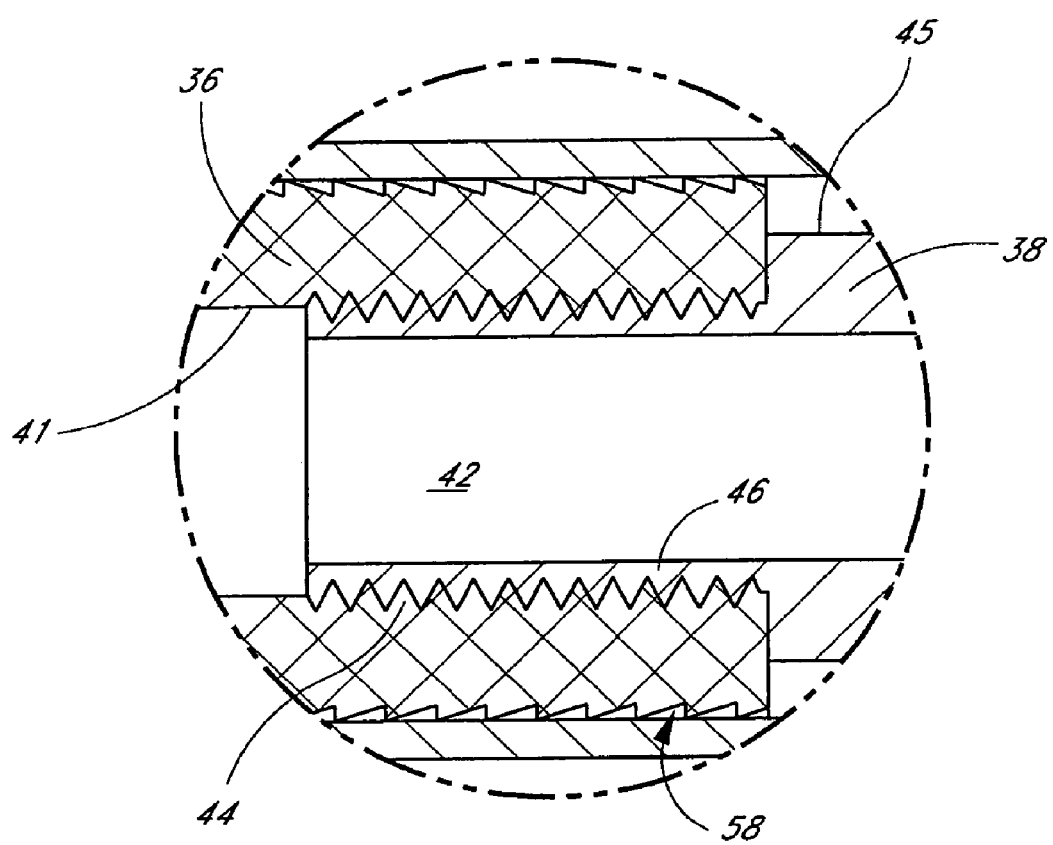
FIG. 7A is an enlarged view of a portion of FIG. 7 labeled 7A-7A.

FIG. 7 illustrates an embodiment in which the body 28 comprises a first portion 36 and a second portion 38 that are coupled together at a junction 40. In the illustrated embodiment, the first portion 36 carries the distal anchor 34 (shown without a central core) while the second portion 38 forms the proximal end 30 of the body 28. As will be explained in more detail below, in certain embodiments, the second portion 38 may be used to pull the body 28 and therefore will sometimes be referred to as a "pull-pin." The first and second portions 36, 38 are preferably detachably coupled to each other at the junction 40. In the illustrated embodiment, the first and second portions 36, 38 are detachably coupled to each other via interlocking threads. Specifically, as best seen in FIG. 7A, the body 28 includes an inner surface 41, which defines a central lumen 42 that preferably extends from the proximal end 30 to the distal end 32 throughout the body 28. At the proximal end of the first portion 36, the inner surface 41 includes a first threaded portion 44. The first threaded portion 44 is configured to mate with a second threaded portion 46, which is located on the outer surface 45 of the second portion 38. The interlocking annular threads of the first and second threaded portions 44, 46 allow the first and second portions 36, 38 to be detachably coupled to each other. In one modified embodiment, the orientation of the first and second threaded portions 44, 46 can be reversed. That is, the first threaded portion 44 can be located on the outer surface of the first portion 36 and the second threaded portion 46 can be located on the inner surface 41 at the distal end of the second portion 38. Any of a variety of other releasable complementary engagement structures may also be used, to allow removal of second portion 38 following implantation, as is discussed below.

In a modified arrangement, the second portion 38 can comprise any of a variety of tensioning elements for permitting proximal tension to be placed on the distal anchor 34 while the proximal anchor is advanced distally to compress the fracture. For example, any of a variety of tubes or wires can be removably attached to the first portion 36 and extend proximally to the proximal handpiece. In one such arrangement, the first portion 36 can include a releasable connector in the form of a latching element, such as an eye or hook. The second portion 38 can include a complementary releasable connector (e.g., a complementary hook) for engaging the first portion 36. In this manner, the second portion 38 can be detachably coupled to the first portion 36 such proximal traction can be applied to the first portion 36 through the second portion as will be explained below. Alternatively, the second portion 48 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein.

In a final position, the distal end of the proximal anchor 50 preferably extends distally past the junction 40 between the first portion 36 and the second portion 38. As explained above, the proximal anchor 50 is provided with one or more surface structures 54 for cooperating with complementary surface structures 58 on the first portion 36 of the body 28.

In this embodiment, the stabilization device 12 may include an antirotation lock (not shown) between the first portion 36 of the body 28 and the proximal collar 50. For example, the first portion 36 may include one or more of flat sides (not shown), which interact with corresponding flat structures in the proximal collar 50. As such, rotation of the proximal collar 50 is transmitted to the first portion 36 and distal anchor 34 of the body 28. Of course, those of skill in the art will recognize various other types of splines or other interfit structures can be used to prevent relative rotation of the proximal anchor and the first portion 36 of the body 28. To rotate the proximal anchor 50, the housing 52 may be provided with a gripping structure (not shown) to permit an insertion tool to rotate the flange proximal anchor 50. Any of a variety of gripping structures may be provided, such as one or more slots, recesses, protrusions, flats, bores or the like. In one embodiment, the proximal end of the proximal anchor 50 is provided with a polygonal, and, in particular, a pentagonal or hexagonal recess or protrusion.

Figure 8:
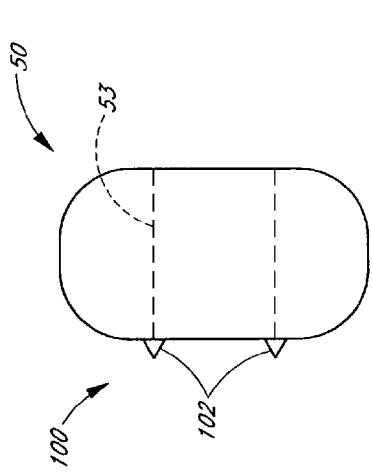
FIG. 8 is a side view of another modified embodiment of the proximal anchor.

With reference to FIG. 8, in a modified embodiment, the distal end of the proximal anchor 50 may include one or more bone engagement features 100, which in the illustrated embodiment comprises a one or more spikes 102 positioned on a contacting surface 104 of the proximal anchors. The spikes 102 provide additional gripping support especially when the proximal anchor 50 is positioned against, for example, uneven bone surfaces and/or soft tissue. In addition, the spikes 102 may limit rotation of the proximal anchor 50 with respect to the body 28 thereby preventing the proximal anchor 50 from backing off the body 28. Other structures for the bone engagement feature 100 may also be used, such as, for example, ridges, serrations etc.

Methods implanting stabilization devices described above as part of a spinal stabilization procedure will now be described. Although certain aspects and features of the methods and instruments described herein can be utilized in an open surgical procedure, the disclosed methods and instruments are optimized in the context of a percutaneous or minimally invasive approach. Thus, the method steps which follow and those disclosed are intended for use in a trans tissue approach. However, to simplify the illustrations, the soft tissue adjacent the treatment site have not been illustrated in the drawings.

In one embodiment of use, a patient with a spinal instability is identified. The patient is preferably positioned face down on an operating table, placing the spinal column into a flexed position. A trocar may then be inserted through a tissue tract and advanced towards a first vertebral body. A guidewire may then be advanced through the trocar and into the first vertebral body. With reference to FIGS. 1A and 1B, the guide wire is preferably inserted into the pedicle of the vertebral body preferably through the pars (i.e. the region of the lamina between the superior and inferior articular processes). A suitable tissue expander may then be inserted over the guidewire and expanded to enlarge the tissue tract. A surgical sheath may then be advanced over the expanded tissue expander.

A drill with a rotatable tip may be advanced over the guidewire and through the sheath. The drill may be used to drill an opening in the vertebral body. The opening may be configured for (i) for insertion of the body 28 of the bone stabilization device 12, (ii) taping and/or (iii) providing a counter sink for the proximal anchor 50. In other embodiments, the step of drilling may be omitted. In such embodiments, the distal anchor 34 is preferably self-tapping and self drilling.

The body 28 of the fixation device may be advanced over the guidewire and through the sheath until it engages the vertebral body. The body 28 may be coupled to a suitable insertion tool prior to the step of engaging the fixation device 12 with the vertebral body. The insertion tool may be configured to engage the coupling 70 on the proximal end of the body 28 such that insertion tool may be used to rotate the body 28. In such an embodiment, the fixation device 12 is preferably configured such that it can also be advanced over the guidewire.

The insertion tool may be used to rotate the body 28 thereby driving the distal anchor 34 to the desired depth within the pedicle of the vertebral body. The proximal anchor 50 may be carried by the fixation device prior to advancing the body 28 into the vertebrae, or may be attached following placement (partially or fully) of the body 28 within the vertebrae. In one embodiment, the clinician will have access to an array of devices 12, having, for example, different diameters, axial lengths, configurations and/or shapes. The clinician will assess the position of the body 28 with respect to the superior vertebral body and chose the proximal anchor 50 from the array, which best fits the patient anatomy to achieve the desired clinical result.

Once the distal anchor 34 is in the desired location, the proximal anchor 50 is preferably advanced over the body 28 until it reaches its desired position. This may be accomplished by pushing on the proximal anchor 50 or by applying a distal force to the proximal anchor 50. In another embodiment, the proximal anchor 50 is advanced by applying a proximal retraction force to the proximal end 30 of body 28, such as by conventional hemostats, pliers or a calibrated loading device, while distal force is applied to the proximal anchor 50. In this manner, the proximal anchor 50 is advanced distally with respect to the body 28 until the proximal anchor 50 is in its proper position (e.g., positioned snugly against the outer surface of the vertebra.) Appropriate tensioning of the stabilization device 12 can be accomplished by tactile feedback or through the use of a calibration device for applying a predetermined load on the stabilization device 12. As explained above, one advantage of the structure of the illustrated embodiments is the ability to adjust compression independently of the setting of the distal anchor 34 within the vertebra.

Following appropriate tensioning of the proximal anchor 50, the proximal portion of the body 28 extending proximally from the proximal anchor 50 can be removed. In one embodiment, this may involve cutting the proximal end of the body 28. For example, the proximal end of the body may be separated by a cutting instrument or by cauterizing. Cauterizing may fuse the proximal anchor 50 to the body 32 thereby adding to the retention force between the proximal anchor 50 and the body 28. Such fusion between the proximal anchor and the body may be particularly advantageous if the pin and the proximal anchor are made from a polymeric or plastic material. In this manner, as the material of the proximal anchor and/or the pin is absorbed or degrades, the fusion caused by the cauterizing continues to provide retention force between the proximal anchor and the body. In another embodiment, the body comprises a first and a second portion 36, 38 as described above. In such an embodiment, the second portion 38 may detached from the first portion 36 and removed. In the illustrated embodiment, this involves rotating the second portion 38 with respect to the first portion via the coupling 70. In still other embodiments, the proximal end of the body 28 may remain attached to the body 28.

The access site may be closed and dressed in accordance with conventional wound closure techniques and the steps described above may be repeated on the other side of the vertebral body for bilateral symmetry as shown in FIGS. 1A and 1B. The bone stabilization devices 12 may be used alone or in combination laminectomy, discectomy, artificial disc replacement, and/or other applications for relieving pain and/or providing stability.

It should be appreciated that not all of the steps described above are critical to procedure. Accordingly, some of the described steps may be omitted or performed in an order different from that disclosed. Further, additional steps may be contemplated by those skilled in the art in view of the disclosure herein, without departing from the scope of the present invention.

With reference to FIGS. 1A and 1B, the proximal anchors 50 of the devices 12 extend above the pars such that they abut against the inferior facet of the superior adjacent vertebrae. In this manner, the proximal anchor 50 forms a wedge between the vertebral bodies limiting compression of the spine as the facet of the superior adjacent vertebrae abuts against the proximal anchor 50. In this manner, compression is limited while other motion is not. For example, flexion, lateral movement and torsion between the superior and inferior vertebral bodies is not limited or constrained. In this manner, the natural motion of the spine can be preserved, especially for those patients with mild or moderate disc conditions. Preferably, the devices are implantable through a minimally invasive procedure and, more preferably, through the use of small percutaneous openings as described above. In this manner, the high cost, lengthy in-patient hospital stays and the pain associated with open procedures can be avoided and/or reduced. In one embodiment, the devices 12 may be removed and/or proximal anchors 50 may be removed in a subsequent procedure if the patient's condition improves. Once implant, it should be appreciated that, depending upon the clinical situation, the proximal anchor 50 may be positioned such that it contacts surfaces of the adjacent vertebrae all of the time, most of the time or only when movement between the adjacent vertebrae exceeds a limit.

In the embodiments described above, it may be advantageous to allow the proximal anchor to rotate with respect to the body 28 thereby preventing the proximal anchor 50 from causing the distal anchor 34 from backing out of the pedicle. In another embodiment, engagement features 100 may be added to the proximal anchor 50 as described above to prevent rotation of the proximal anchor 50.

The fixation devices 12 may be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material.

In one embodiment, the proximal anchor 50 is formed, at least in part, from an elastic and/or resilient material. In this manner, the shock and forces that are generated as the proximal anchor abuts or wedges against the inferior articular process of the superior adjacent vertebrae can be reduced or dissipated. In one such embodiment, the proximal anchor 50 is formed in part by a polycarbonate urethane or a hydrogel. In such embodiments, the elastic material may be positioned on the outer surfaces of the proximal anchor or the portions of the outer surfaces that abut against the surfaces of the inferior articular process of the superior adjacent vertebrae.

Figure 9A:
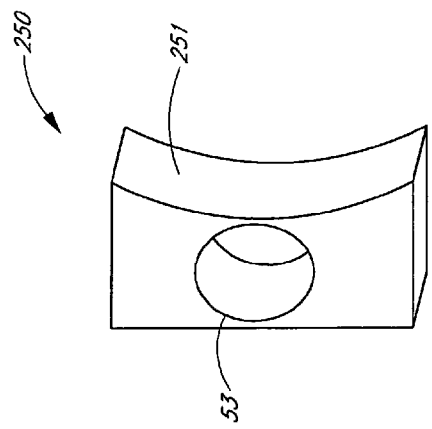
FIG. 9A is a side view of another modified embodiment of the proximal anchor.
Figure 9:
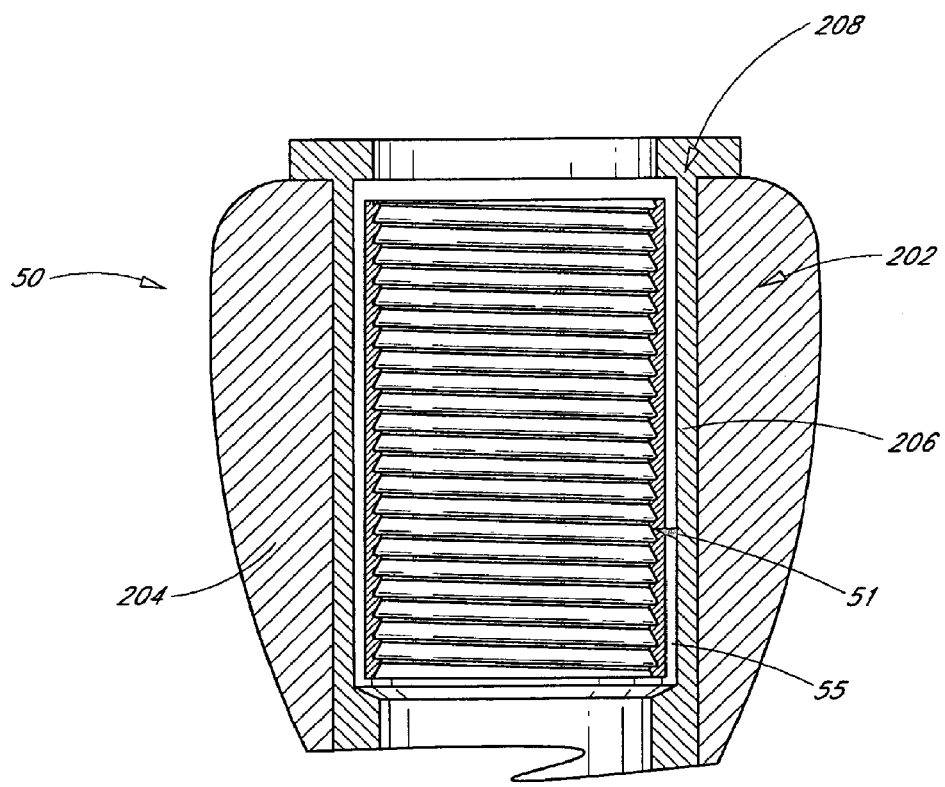
FIG. 9 is a top perspective view of a modified embodiment of the proximal anchor.

For example, FIG. 9 illustrates an embodiment of a proximal anchor 50', which comprises an outer housing or shell 202. The shell 202 may be formed or a resilient material such as, for example, a biocompatible polymer. The proximal anchor 50' also comprises an inner member 204 that comprises a tubular housing 206 and a proximal flange 208. The inner member 202 is preferably formed of a harder more rugged material as compared to the shell 202, such as, for example, titanium or another metallic material. The shell 202 is fitted or formed over the tubular housing 206. When deployed, the shell 202 is held in place between the flange 208 and the surface of the vertebrae in which the body 202 is placed. In modified embodiments, the shell 202 may be coupled to the inner member 204 in a variety of other manners, such as, adhesives, fasteners, interlocking surfaces structures and the like. In the illustrated embodiment, the inner member 204 includes a locking ring 51 positioned within a recess 55 as described above. Of course, in modified embodiments, other retention structures 54 and complementary retention structures 58 may be used between the body 28 and the proximal anchor 50' to permit distal axial travel of the proximal anchor 50' with respect to the body 28, but resist proximal travel of the proximal anchor 50' with respect to the body 28.

Figure 10:
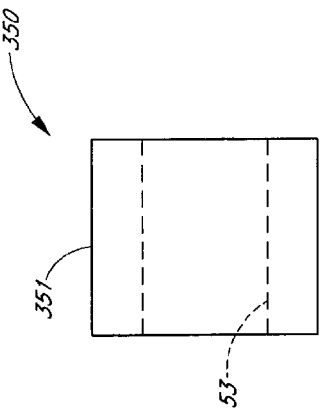
FIG. 10 is a side view of another modified embodiment of the proximal anchor.

FIGS. 9A and 10 illustrate modified shapes of the proximal anchor which can be used alone or in combination with the elastic or resilient material described above. In FIG. 9A, the proximal anchor 250 has a saddle shaped curved surface 251 that generally faces the inferior articular process of the superior adjacent vertebrae. In this embodiment, the saddle shaped surface may limit compression of the adjacent vertebral bodies and limit side to side motion and/or torsion between the vertebral bodies. FIG. 10 illustrates an embodiment in which the proximal anchor 350 has a rectangular shape with a flat shaped surface 351. In this embodiment, the flat shaped surface may limit compression of the adjacent vertebral bodies and limit side to side motion between the vertebral bodies. In the embodiments of FIGS. 9A and 10, in may be advantageous to limit or eliminate any rotation of the proximal anchor 50 with respect to the body 28 and/or the vertebral body. As such, the proximal anchor 50 preferably includes the retention devices 100 described above with reference to FIG. 8.

The above described devices and techniques limit motion of the spine by providing an abutment or wedge surface on one vertebral body. The abutment surface contacts a portion of a second, adjacent vertebral body so as limit least one degree of motion between the two vertebral bodies while permitting at least one other degree of motion. While the above described devices and techniques are generally preferred, certain features and aspects can be extended to modified embodiments for limiting motion between vertebral bodies. These modified embodiments will now be described.

In one embodiment, the proximal anchor 50 of the fixation device may be, coupled to attached or integrally formed with the body 28. In this manner, movement between the proximal anchor 50 and the body 28 is not permitted. Instead, the clinician may chose a fixation device of the proper length and advance the device into the vertebral body until the proximal anchor lies flush with the vertebral body or is otherwise positioned accordingly with respect to the vertebral body.

In another embodiment, the abutment surface may be attached to the vertebral body through the use of an adhesive, fasteners, staples, screws and the like In still another embodiment, the abutment surface may formed on a distal end of a stabilization device that is inserted through the front side of the vertebral body.

Preferably, the clinician will have access to an array of fixation devices 12, having, for example, different diameters, axial lengths and, if applicable, angular relationships. These may be packaged one or more per package in sterile or non-sterile envelopes or peelable pouches, or in dispensing cartridges which may each hold a plurality of devices 12. The clinician will assess the dimensions and load requirements, and select a fixation device from the array, which meets the desired specifications.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. In another embodiment, the body is made of PEEK™ polymer or similar plastic material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:
1. A spinal stabilization device comprising:
an elongate body having a proximal end and a distal end;
a distal anchor on the distal end of the elongate body;

a retention structure on the body, proximal to the distal anchor;

a proximal anchor including one or more spikes positioned on a contacting surface of the proximal anchor, the one or more spikes configured to limit rotation of the proximal anchor with respect to the elongate body when the proximal anchor is positioned against bone or tissue; and at least one complementary retention structure on the proximal anchor configured to permit distal movement of the proximal anchor with respect to the elongate body but resist proximal movement of the proximal anchor with respect to the elongate body.

2. The spinal stabilization device of claim 1, wherein the contacting surface is located on a distal end of the proximal anchor.

3. The spinal stabilization device of claim 1, wherein the elongate body is cannulated.

4. The spinal stabilization device of claim 1, wherein the proximal anchor comprises a lumen configured such that the elongate body may extend, at least partially, through the proximal anchor.

5. The spinal stabilization device of claim 4, wherein the complementary retention structure is formed by an annular ring, which is positioned within an annular recess formed along the lumen.

6. The spinal stabilization device of claim 1, wherein the proximal anchor is configured to be distally moveable along the elongate body to permit compression between a distal end and a proximal end of the spinal stabilization device.

7. The spinal stabilization device of claim 1, wherein the distal anchor comprises a helical flange.

8. The spinal stabilization device of claim 1, wherein the retention structure on the elongate body and the at least one complementary retention structure on the proximal anchor comprise a series of ridges or grooves.

9. A spinal stabilization device comprising:
an elongate body having a proximal end and a distal end;
a distal anchor on the distal end of the elongate body;
a retention structure on the elongate body, proximal to the distal anchor;
a proximal anchor including one or more serrations, the one or more serrations configured to provide additional gripping support when the proximal anchor is positioned against uneven bone surfaces or soft tissue; and
at least one complementary retention structure on the proximal anchor configured to permit distal movement of the proximal anchor with respect to the elongate body but resist proximal movement of the proximal anchor with respect to the elongate body.

10. The spinal stabilization device of claim 9, wherein the one or more serrations are located on a distal end of the proximal anchor.

11. The spinal stabilization device of claim 9, wherein the elongate body is cannulated.

12. The spinal stabilization device of claim 9, wherein the proximal anchor comprises a lumen configured such that the elongate body may extend, at least partially, through the proximal anchor.

13. The spinal stabilization device of claim 12, wherein the complementary retention structure is formed by an annular ring, which is positioned within an annular recess formed along the lumen.

14. The spinal stabilization device of claim 9, wherein the proximal anchor is configured to be distally moveable along the elongate body to permit compression between a distal end and a proximal end of the spinal stabilization device.

15. The spinal stabilization device of claim 9, wherein the distal anchor comprises a helical flange.

16. The spinal stabilization device of claim 9, wherein the retention structure on the elongate body and the at least one complementary retention structure on the proximal anchor comprise a series of ridges or grooves.

17. A spinal stabilization device comprising:
an elongate body having a proximal end and a distal end;
a distal anchor on the distal end of the elongate body;
a retention structure on the elongate body, proximal to the distal anchor; and
a proximal anchor including one or more bone engagement features, the one or more bone engagement features positioned on the distal end of the proximal anchor, the one or more bone engagement features configured to provide additional gripping support of the proximal anchor and limit rotation of the proximal anchor with respect to the elongate body; and
at least one complementary retention structure on the proximal anchor configured to permit distal movement of the proximal anchor with respect to the elongate body but resist proximal movement of the proximal anchor with respect to the elongate body.

18. The spinal stabilization device of claim 17, wherein the one or more bone engagement features are selected from the group consisting of spikes, ridges, and serrations.

19. The spinal stabilization device of claim 17, wherein the proximal anchor comprises a lumen configured such that the elongate body may extend, at least partially, through the proximal anchor.

20. The spinal stabilization device of claim 19, wherein the complementary retention structure of the proximal anchor is formed by an annular ring, which is positioned within an annular recess formed along the lumen.

* * * * *